(12) United States Patent
Dees et al.

(10) Patent No.: US 6,991,776 B2
(45) Date of Patent: *Jan. 31, 2006

(54) INTRACORPOREAL MEDICAMENTS FOR HIGH ENERGY PHOTOTHERAPEUTIC TREATMENT OF DISEASE

(75) Inventors: H. Craig Dees, Knoxville, TN (US); Timothy C. Scott, Knoxville, TN (US); Eric A. Wachter, Oak Ridge, TN (US); Walter G. Fisher, Knoxville, TN (US); John Smolik, Loudon, TN (US)

(73) Assignee: Xantech Pharmaceuticals, Inc., Knoxville, TN (US)

( * ) Notice: Subject to any disclaimer, the term of this patent is extended or adjusted under 35 U.S.C. 154(b) by 65 days.

This patent is subject to a terminal disclaimer.

(21) Appl. No.: 10/331,854

(22) Filed: Dec. 30, 2002

(65) Prior Publication Data

US 2003/0125376 A1    Jul. 3, 2003

Related U.S. Application Data

(60) Division of application No. 09/817,448, filed on Mar. 26, 2001, and a continuation-in-part of application No. 09/216,787, filed on Dec. 21, 1998, now Pat. No. 6,331,286.

(60) Provisional application No. 60/195,090, filed on Apr. 6, 2000.

(51) Int. Cl.
*A61K 51/00* (2006.01)

(52) U.S. Cl. .......................... 424/1.85; 435/6; 435/7.21; 435/7.23; 436/813; 436/819; 424/1.69; 424/1.89; 424/9.321; 514/2; 514/12; 514/13; 514/14; 514/73; 514/78; 530/388.2; 530/388.8; 530/388.85; 530/389.7

(58) Field of Classification Search ................... 435/6, 435/7.21, 7.23; 436/813, 819; 424/1.69, 424/185, 1.89, 9.321, 1.85; 514/2, 12, 13, 514/14, 73, 78; 530/388.2, 388.8, 388.85, 530/389.7

See application file for complete search history.

(56) References Cited

U.S. PATENT DOCUMENTS

| | | | |
|---|---|---|---|
| 4,647,578 A | 3/1987 | Crounse et al. | |
| 4,846,789 A | 7/1989 | Heitz et al. | |
| 5,552,452 A | 9/1996 | Khadem et al. | |
| 6,331,286 B1 * | 12/2001 | Dees et al. | ............... 424/1.85 |

FOREIGN PATENT DOCUMENTS

| | | |
|---|---|---|
| WO | WO 99/45869 | 6/1999 |
| WO | WO 00/25665 | 5/2000 |
| WO | WO 00/43045 | 7/2000 |

OTHER PUBLICATIONS

Search Report for Application No. EP 01 92 6602 dated May 14, 2003.
Office Action dated Dec. 3, 2004 for U.S. Appl. No. 09/817,448.
Wilson et al., "Enhancement of Tumor Radiation Response by the Anivascular Agent 5,6-Dimethylxanthenone-4-Acetic Acid," Int. J. Radiation Oncology Biol. Phys., vol. 42, No. 4, pp. 905-908, (1998).

* cited by examiner

*Primary Examiner*—Long V. Le
*Assistant Examiner*—Gailene R. Gabel
(74) *Attorney, Agent, or Firm*—Cook, Alex, McFarron, Manzo, Cummings & Mehler, Ltd.

(57) ABSTRACT

New intracorporeal radiodense medicaments and certain medical uses and methods for use of such high energy phototherapeutic medicaments for treatment of human or animal tissue are described, wherein a primary active component of such medicaments is a halogenated xanthene or halogenated xanthene derivative. The halogenated xanthenes constitute a family of potent radiosensitizers that become photoactivated upon irradiation of the treatment site with ionizing radiation. In embodiments of the present invention, such medicaments are used for treatment of a variety of conditions affecting the skin and related organs, the mouth and digestive tract and related organs, the urinary and reproductive tracts and related organs, the respiratory tract and related organs, the circulatory system and related organs, the head and neck, the endocrine and lymphoreticular systems and related organs, various other tissues, such as connective tissues and various tissue surfaces exposed during surgery, as well as various tissues exhibiting microbial or parasitic infection. In another embodiment, such medicaments are produced in various formulations including liquid, semisolid, solid or aerosol delivery vehicles.

4 Claims, 2 Drawing Sheets

INTRACORPOREAL MEDICAMENTS FOR HIGH ENERGY PHOTOTHERAPEUTIC TREATMENT OF DISEASE

CROSS REFERENCE TO RELATED APPLICATION

This application is a divisional application of copending U.S. application Ser. No. 09/817,448 filed on Mar. 26, 2001 which is based on provisional application U.S. Ser. No. 60/195,090 filed Apr. 6, 2000 and is a continuation-in-part of U.S. Ser. No. 09/216,787 (entitled "High Energy Phototherapeutic Agents"), filed on Dec. 21, 1998, now U.S. Pat. No. 6,331,286 issued Dec. 18, 2001, which is herein incorporated by reference in its entirety.

BACKGROUND OF THE INVENTION

1. Field of the Invention

The present invention is directed to certain radiodense medicarnents and methods for treatment of human or animal tissue using such medicaments in combination with radiation therapy, wherein these radiodense medicaments serve as radiosensitizers in high energy phototherapy. The inventors of the present invention have found that such medicaments are useful for treatment of a variety of conditions affecting the skin and related organs, the mouth and digestive tract and related organs, the urinary and reproductive tracts and related organs, the respiratory tract and related organs, the circulatory system and related organs, the head and neck, the endocrine and lymphoreticular systems and related organs, various other tissues, such as connective tissues and various tissue surfaces exposed during surgery, as well as various tissues exhibiting microbial, viral, fungal or parasitic infection. These medicaments are in various formulations that may include liquid, semisolid, solid or aerosol delivery vehicles, and are suitable for intracorporeal administration via various conventional modes and routes, including intravenous injection (i.v.), intraperitoneal injection (i.p.), intramuscular injection (i.m.), intracranial injection (i.c.), intratumoral injection (i.t.), intraepithelial injection (i.e.), transcutaneous delivery (t.c.), and per oesophageal (p.o.) administration. Irradiation of tissues containing such medicaments with ionizing radiation produces adesirable therapeutic response, such as destruction of microbial infection, reduction or elimination of tissue irritation, reduction or elimination of hyperproliferative tissue, reduction or elimination of cancerous or precancerous tissue, reduction or elimination of surface or subsurface lipocytes or lipid deposits, and many other similar indications.

2. Description of the Related Art

Diseased tissue or tumors, such as those of cancer, are often treated using high energy, highly penetrating ionizing radiation (i.e., ionizing radiation, or radiation), in a process known as radiation therapy.

Conventional radiation therapy (which typically uses ionizing radiation with energies of 1 keV or higher) generally works by attacking rapidly growing cells with ionizing radiation. Use of such radiation is attractive due to its ability to penetrate deeply into tissue, especially when diseased tissue consists of, or is located within, bone or other dense or opaque structures. Unfortunately, using rapid growth as the sole targeting criterion does not limit the effects of such treatment to diseased tissue, and as a result, heathy tissue is often destroyed or damaged.

As a result, some improvements have been made in the methods for delivery of the radiation to the disease site so as to limit the effects of such radiation to the general area of the diseased tissue. However, since healthy tissue and diseased tissue typically have a similar biological response to ionizing radiation, a need exists to improve the potency of (or biological response to) the delivered radiation within the vicinity of the diseased tissue to the diseased tissue, so as to not affect the surrounding healthy tissue.

Accordingly, some investigators have focused their efforts on developing agents that become activated by, or increase the therapeutic potential of, such ionizing radiation. Such agents are known as radiosensitizers, and when used in combination with ionizing radiation constitute a therapeutic modality known as high energy phototherapy. Since radiosensitizers function by absorbing or otherwise interacting with penetrating, ionizing radiation and locally transforming this radiation into a more biologically active form, it is desirable that such radiosensitizer agents exhibit high intrinsic radiodensity and a capacity for preferential concentration in diseased tissue (thus allowing maximal, selective delivery of the therapeutic effects of such radiation to such diseased tissue containing such agent).

Due to the focal nature of many diseases, it is desirable to achieve this preferential concentration of the radiosensitizer through natural processes or via localized application of agent. The desired result is then for radiation to become more efficacious when the radiosensitizer is present in tissue, so that less radiation is needed to treat the lesion, tumor or other diseased tissue, and accordingly, potential damage to surrounding healthy tissue, resulting from collateral exposure to the radiation, is reduced. Hence, safety and efficacy can be improved by having agents capable of preferential concentration in diseased tissue.

The ultimate success or failure of high energy phototherapy thus depends on: (1) therapeutic performance of radiosensitizer agents, and (2) disease specificity in delivery of agents to the site of disease or diseased tissue. Currently used agents and targeting approaches, however, have had unacceptable results in each of these categories.

The therapeutic performance of a radiosensitizer is a function of enhanced absorption of the applied radiation dose in sensitized tissues relative to that in non-sensitized tissues. This differential absorption is commonly effected by use of radiodense agents having a high absorption cross-section for a particular type of radiation (such as x-rays). For example, metal or halogen atoms are often used, either in atomic form or incorporated into a molecular carrier, due to their high x-ray cross-section. Absorption of x-rays by such radiodense materials appears to lead to secondary radiative emissions, ionization, and other chemical or physical processes that increase the localized cytotoxicity of the applied energy (i.e., radiation-induced cell death, or "light cytotoxicity").

However, a high light cytotoxicity is not enough to make an agent an acceptable agent. The agent must also have a negligible effect when energy is not applied (i.e., have a low toxicity in the absence of radiation, or "dark cytotoxicity"). Unfortunately, many agents presently under investigation as radiosensitizers are disadvantageous as they either have (a) a relatively high dark cytotoxicity or (b) a low light (cytotoxicity)-to-dark cytotoxicity ratio which limits their effectiveness and acceptability. In contrast, agents having a high light-to-dark cytotoxicity ratio are desirable because they (1) can be safely used over a range of dosages, (2) will exhibit improved efficacy at the treatment site (due to the compatibility with use at higher dosages as a consequence of their relative safety), and (3) will be better tolerated throughout the patient's body.

An additional problem with many current radiosensitizers is that the agent does not achieve significant preferential concentration in diseased tissue. Specifically, most radiosensitizer targeting has been based on physical targeting, such as diffusion into tumors through leaky neovasculature, which ultimately succeeds or fails based on permeability of the tumor to agents that are aqueously soluble or are in a suspension formulation. As a result, large doses of the agent typically need to be administered, either locally or systemically, so as to saturate all tissues, hopefully reaching a therapeutic level in the desired treatment region or target. After such agent administration, a patient has to wait a clearance time of from hours to days to allow excess agent to hopefully clear from the healthy tissues surrounding the desired treatment site. Thereafter, irradiation of residual agent at the treatment site hopefully produces the desired therapeutic effect in the diseased tissue. This approach unfortunately can also damage healthy surrounding tissue by undesired activation of residual agent still present in the healthy surrounding tissue. One approach to solving this problem is to couple the radiosensitizer with a moiety capable of providing improved biotargetting of the diseased tissue. This, however, has proven to be very difficult to achieve.

It would also be highly desirable if the radiosensitizer could be used to improve identification of target size, location and depth so that the therapeutic radiation could be more precisely delivered to the target, such as to a cancerous tumor. Further, combined diagnostic use (as a contrast agent) and therapeutic use (as a radiosensitizer) of the agent would reduce risk to the patient by (1) reducing the number of required procedures necessary for diagnosis and treatment, (2) reducing the overall diagnosis and treatment time, and (3) reducing cost.

Thus, the inherent disadvantages of various current radiosensitizer agents and medicaments containing such agents have made acceptable radiation therapy for various human and animal conditions difficult or impossible.

Therefore, it is an object of the present invention to provide new intracorporeal radiodense medicaments, medical uses for such medicaments based on improved specificity of such medicaments for the desired tissue to be treated, and methods for treatment using such medicaments, thereby resulting in increased efficacy and safety and reduced cost of treatment.

SUMMARY OF THE PRESENT INVENTION

The present invention is directed to new intracorporeal radiodense medicaments and certain medical uses of such medicaments, and methods for treatment using such medicaments, for treatment of human or animal tissue, wherein a primary active component of such medicaments is a halogenated xanthene or a halogenated xanthene derivative, and more preferably Rose Bengal or a functional derivative of Rose Bengal. The halogenated xanthenes constitute a family of potent radiosensitizers that are activated upon irradiation of the treatment site with ionizing radiation, such as x-rays. Such medicaments are suitable for intracorporeal administration, and are thus intracorporeal medicaments. Such medicaments can also be called pharmaceutical compositions or agents.

In a preferred embodiment, such medicaments are used for high energy phototherapeutic treatment of a variety of conditions affecting the skin and related organs.

In another preferred embodiment, such medicaments are used for high energy phototherapeutic treatment of a variety of conditions affecting the mouth and digestive tract and related organs.

In another preferred embodiment, such medicaments are used for high energy phototherapeutic treatment of a variety of conditions affecting the urinary and reproductive tracts and related organs.

In another preferred embodiment, such medicaments are used for high energy phototherapeutic treatment of a variety of conditions affecting the respiratory tract and related organs.

In another preferred embodiment, such medicaments are used for high energy phototherapeutic treatment of a variety of conditions affecting the circulatory system and related organs.

In another preferred embodiment, such medicaments are used for high energy phototherapeutic treatment of a variety of conditions affecting the head and neck.

In another preferred embodiment, such medicaments are used for high energy phototherapeutic treatment of a variety of conditions affecting the endocrine and lymphoreticular systems and related organs.

In another preferred embodiment, such medicaments are used for high energy phototherapeutic treatment of a variety of conditions affecting various other tissues, such as connective tissues and various tissue surfaces exposed during surgery.

In another preferred embodiment, such medicaments are used for high energy phototherapeutic treatment of a variety of conditions related to microbial or parasitic infection.

In another preferred embodiment, such medicaments are produced in various formulations including liquid, semi-solid, solid or aerosol delivery vehicles, as well as in tablet, capsule, suppository and other similar forms.

BRIEF DESCRIPTION OF THE DRAWINGS

In describing the preferred embodiments, reference is made to the accompanying drawings wherein.

DETAILED DESCRIPTION OF THE PRESENTLY PREFERRED EMBODIMENTS

Figure 1A:
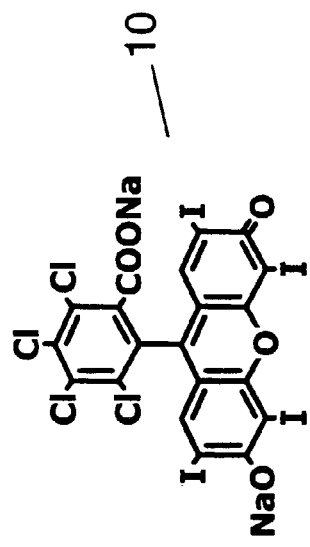
FIG. 1(a) shows the generalized chemical structure of the halogenated xanthenes.

The present invention is directed to new radiodense medicaments and certain medical uses of such radiodense medicaments, and methods for high energy phototherapeutic treatment using such medicaments, for treatment of human or animal tissue, wherein a primary active component of such medicaments is a halogenated xanthene or halogenated xanthene derivative. The inventors of the present invention have discovered that such halogenated xanthenes, as discussed in more detail infra, exhibit desirable high energy phototherapeutic effects when applied to or otherwise delivered to certain human or animal tissues. The desirable effects include reduction or elimination of disease or diseased tissue or other undesirable conditions, including eradication of cancerous or pre-cancerous tumors and infectious agents, and are applicable to a variety of conditions affecting the skin and related organs, the mouth and digestive tract and related organs, the urinary and reproductive tracts and related organs, the respiratory tract and related organs, the circulatory system and related organs, the head and neck, the endocrine and lymphoreticular systems and related organs, various other tissues, such as tissues exposed during surgery, as well as various tissues exhibiting microbial, viral, fungal or parasitic infection.

In a preferred embodiment, such medicaments are produced in various formulations suitable for intracorporeal administration, including in various liquid, semisolid, solid or aerosol delivery vehicles, as well as in tablet, capsule, suppository, and other similar forms. Such medicament formulations are suitable for delivery via various conventional modes and routes (hereafter defined as intracorporeal administration), including, but not limited to, intravenous injection (i.v.), intraperitoneal injection (i.p.), intramuscular injection (i.m.), intracranial injection (i.c.), intratumoral injection (i.t.), intraepithelial injection (i.e.), transcutaneous delivery (t.c.), and per oesophageal (p.o.) administration; additional administrative modes and routes include intraabdominal, intraapendicular, intraarterial, intraarticular, intrabronchial, intrabuccal, intracapsular, intracardial, intracartilaginous, intracavitary, intracephalic, intracolic, intracutaneous, intracystic, intradermal, intraductal, intraduodenal, intrafascicular, intrafat, intrafilar, intrafissural, intragastric, intraglandular, intrahepatic, intraintestinal, intralamellar, intralesional, intraligamentous, intralingual, intramammary, intramedullary, intrameningeal, intramyocardial, intranasal, intraocular, intraoperative, intraoral, intraosseous, intraovarian, intrapancreatic, intraparietal, intrapelvic, intrapericardial, intraperineal, intraperitoneal, intraplacental, intrapleural, intrapontine, intraprostatic, intrapulmonary, intrarachidian, intrarectal, intrarenal, intrascleral, intrascrotal, intrasegmental, intrasellar, intraspinal, intrasplenic, intrasternal, intrastromal, intrasynovial, intratarsal, intratesticular, intrathoracic, intratonsillar, intratracheal, intratubal, intratympanic, intraureteral, intraurethral, intrauterine, intravaginal, intravascular, intraventricular, intravertebral, intravesical, or intravitreous administration. Such medicaments will thus be referred to as intracoporeal medicaments (i.e., medicaments suitable for intracorporeal administration).

1. Properties of the Preferred Radiodense Components and Medicament Formulations.

The inventors of the present invention have discovered a class of radiodense agents that are broadly applicable for producing intracoporeal medicaments for high energy phototherapeutic treatment of disease in certain human and animal tissues. These radiodense agents are referred to as halogenated xanthenes and are illustrated in FIG. 1a, where the symbols X, Y, and Z represent various elements present at the designated positions, and the symbols $R^1$ and $R^2$ represent various functionalities present at the designated positions. The halogen content of the halogenated xanthenes makes this class of agent highly efficient absorbers of x-rays or other ionizing radiation of energy greater than approximately 1 keV and less than approximately 1000 MeV, and thus suitable as radiodense components in various radiosensitizer medicaments used in conjunction with such radiation in high energy phototherapy.

Selected chemical and physical properties (such as chemical constituents at positions X, Y, and Z and functionalities $R^1$ and $R^2$, along with molecular weight) of representative halogenated xanthenes are summarized in attached Table 1 (infra). Certain general properties of this class of agents are discussed in further detail in U.S. Ser. No. 09/130,041, filed on Aug. 6, 1998 (entitled "Improved Method for Targeted Treatment of Disease"); U.S. Ser. No. 09/184,388, filed on Nov. 2, 1998 (entitled "Method for Improving Imaging and Photodynamic Therapy"); U.S. Ser. No. 09/216,787, filed on Dec. 21, 1998; (entitled "High Energy Phototherapeutic Agents"); and U.S. Ser. No. 60/149,015, filed on Aug. 13, 1999 (entitled "Improved Topical Medicaments and Methods for Photodynamic Treatment of Disease"), each of which are herein incorporated by reference in their entirety. In general, the halogenated xanthenes are characterized by a large radiation absorbance cross-section, low dark cytotoxicity (toxicity to cells or tissues in the absence of radiation), high light cytotoxicity (toxicity to cells or tissues' upon irradiation), relatively low cost, an ability to clear rapidly from the body, and chemical and radiosensitizer properties that are substantially unaffected by the local chemical environment or the attachment of functional derivatives at positions $R^1$ and $R^2$. The halogenated xanthenes also exhibit a preference for concentration in diseased tissue, and thus are capable of exhibiting enhanced radiation dose enhancement over that possible with previously known agents. These special properties of the halogenated xanthenes, and in particular intracorporeal medicaments formulated from such agents, make such agents and medicaments excellent for high energy phototherapeutic treatment of disease in human and animal tissues.

Figure 1B:
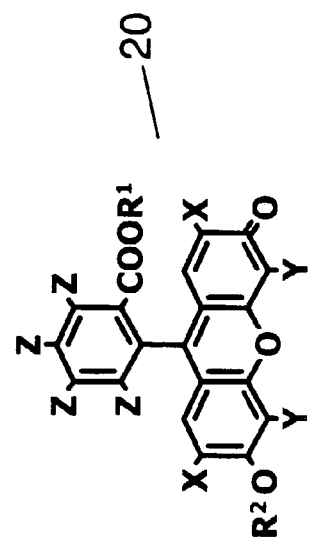
FIG. 1(b) shows the chemical structure of Rose Bengal.
Figure 2:
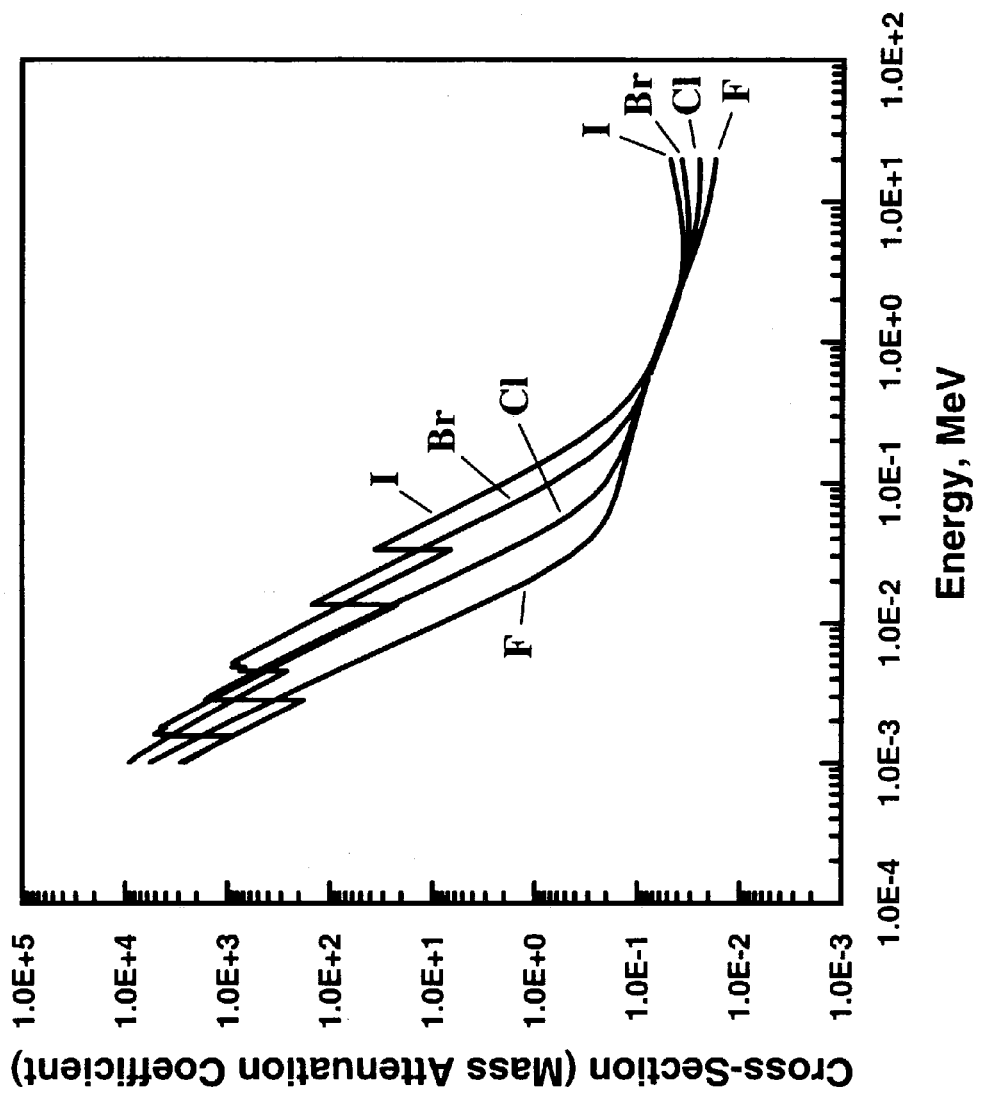
FIG. 2 is a graph of energy versus x-ray cross-section for halogens.

One preferred embodiment of an intracorporeal medicament according to the present invention contains a radiodense ingredient, at a concentration of from greater than approximately 0.001% to less than approximately 20%, comprised of at least one halogenated xanthene, including for example one or more of: 4,5'-Dichlorofluorescein; 2',7'-Dichlorofluorescein; 4,5,6,7-Tetrachlorofluorescein; 2',4',5',7'-Tetrachlorofluorescein; Dibromofluorescein; Solvent Red 72; Diiodofluorescein; Eosin B; Eosin Y; Ethyl Eosin; Erythrosin B; Phloxine B; Rose Bengal (4,5,6,7-tetrachloro-2',4',5',7'-tetraiodofluorescein; shown in FIG. 1b); 4,5,6,7-Tetrabromoerythrosin; Mono-, Di-, or Tribromoerythrosin; Mono-, Di-, or Trichloroerythrosin; Mono-, Di-, or Trifluoroerythrosin; 2,7'-Dichloro-4,5,6,7-Tetrafluorofluorescein; 2',4,5,6,7,7'-Hexafluorofluorescein; and 4,5,6,7-Tetrafluorofluorescein. Since the radiation cross-section of halogens increases substantially in the order F<Cl<Br<I (as shown in FIG. 2), it is further preferred that this medicament include, as a radiodense ingredient, those halogenated xanthenes with a large content of I or Br. As shown in Table 1 (Infra), Tetrabromoerythrosin, Rose Bengal, Phloxine B, Erythrosin B, and Eosin Y have large I or Br contents relative to other halogenated xanthenes, and thereby are more preferred for use as a radiodense ingredient in such medicaments. Further, the high iodine content of Rose Bengal and its derivatives and the additional bromine substitution of 4,5,6,7-Tetrabromoerythrosin and its derivatives, make these agents even more preferrable for use as a radiodense ingredient in such medicaments.

The inventors of the present invention have found that intracorporeal medicaments that contain, as a radiodense ingredient, at least one halogenated xanthene, exhibit preferential accumulation of said radiodense ingredient in diseased tissue. Such accumulation of said radiodense ingredient within or in physical proximity to such tissue increases the efficiency of radiosensitization of such tissue (i.e., conversion of applied ionizing radiation into localized cytotoxic effects in or near such tissue). This yield enhancement is believed to result from the increased probability that proximally-released energy (i.e., scattered or otherwise re-emitted energy released upon interaction of applied ionizing radiation with said radiosensitizer) will interact favorably with the target tissue (before annihilating or otherwise dissipating in an inefficacious manner) whenever said radiodense ingredient responsible for such released energy is concentrated as close as possible to such target tissue. Stated in simple terms, the released energy, generally having a short mean free path, has a higher probability of interacting with target tissue if it is released from a radiodense ingredient that has been delivered to a location within or close to the target tissue.

For example, it is possible to estimate an agent's potential for tissue accumulation based on the partition coefficient, $K_p$. This in vitro parameter is commonly purported to have predictive value relating to in vivo agent delivery at the cellular level. In particular, a value greater than unity is considered to indicate agents capable of localizing in tumor or other diseased tissue, and more specifically in plasma membranes of cells composing such tissue, and thereby being capable of exhibiting enhanced therapeutic efficacy in such tissue. $K_p$ is determined by measuring the ratio of equilibrium concentrations of an agent in a lipophilic phase (n-octanol) contacted with an aqueous phase (saline). Comparative values of $K_p$ are shown in Table 2 (infra). The large $K_p$ values for the halogenated xanthenes indicate that the halogenated xanthenes will exhibit a tendency to accumulate in tumor or other diseased tissue, and should thereby be capable of exhibiting superior high energy phototherapeutic efficacy in such tissue.

A specific example of such preferential accumulation and therapeutic response of the halogenated xanthenes in diseased tissue is exhibited by Rose Bengal. In particular, the inventors of the present invention have found that Rose Bengal will accumulate preferentially in (i.e., target) some tumors and other diseased tissues. This preference for accumulation in diseased tissue is illustrated by the following examples which we meant to illustrate and not limit the present invention:

Initially, tumor cell suspensions (for example, melanoma, breast tumor, liver tumor, renal carcinoma, gall bladder tumor or prostate tumor) were injected subcutaneously into the flanks of nude mice resulting in formation of primary tumors, within a few weeks, at the injection site having a tumor volume of approximately 0.5–1 cm$^3$.

Thereafter, a solution of Rose Bengal (for example, ≦100 μL of 10% Rose Bengal in saline) was intratumorally injected, followed by therapeutic irradiation of the tumor within several hours post administration using x-rays (for example, 10 Gy at 120 keV) or gamma rays (for example, 4–10 Gy at 1.02 MeV). This resulted in selective destruction of tumor tissue with no substantive effect in healthy surrounding tissue.

In addition, the inventors of the present invention discovered that intratumoral injection (i.t., of various Rose Bengal formulations in the other model tumors (i.e., breast tumor, liver tumor, renal carcinoma, gall bladder tumor or prostate tumor) resulted in similar persistent accumulation of Rose Bengal throughout the tumor volume, with more than 75% of the injected Rose Bengal dose remaining in the tumor after several weeks. Peritumoral injection (i.e., injection into normal tissue around the outside margins of the tumor) exhibited no such persistence in normal tissue, with less than 1% of Rose Bengal remaining in the vicinity of the tumor after 24 hours.

Thus, the inventors of the present invention have shown that medicaments containing at least one halogenated xanthene, and in particular Rose Bengal, exhibit a marked preference for accumulation in tumor and other diseased tissue upon intracorporeal administration, and that once present in such tissue, said medicaments can be utilized as potent, highly tissue specific radiosensitizers.

In addition to superior suitability for direct administration into desired tissue to be treated such as a focal tumor, the preference of the halogenated xanthenes for accumulation in certain tissues provides a basis for highly-selective, systemic delivery of the halogenated xanthenes to such tissues. For example, Rose Bengal's relatively large partition coefficient is indicative of a preference for accumulation in lipophilic tissue, such as cutaneous lipocytes. The inventors of the present invention have found that systemic administration of Rose Bengal, for example as an aqueous solution administered via intraperitoneal injection (i.p.) or per oesophagus (p.o.), resulted in highly selective accumulation of said agent in certain tissues, such as in the cutaneous fat deposits of obese laboratory mice. Histologic examination of skin samples from such animals shows that the accumulated agent is substantively limited to cutaneous lipocytes. Furthermore, activation of this accumulated agent precipitates selective destruction of such lipocytes with no effect in overlying skin or underlying muscle tissue.

Moreover, the inventors of the present invention have discovered that the facility with which the halogenated xanthenes target specific tissues or other sites can be further optimized by attachment of specific functional derivatives at positions $R^1$ and $R^2$, so as to change the chemical partitioning or biological activity of the agent. For example, attachment of one targeting moiety or more at positions $R^1$ or $R^2$ can be used to improve targeting to specific tissues, such as cancerous tumor tissues or sites of localized infection. An example of this is esierification at position $R^1$ with a short aliphatic alcohol such as ethanol or n-hexanol, to produce a derivatized agent exhibiting enhanced partitioning into lipid-rich tumor tissues.

It is thus a further embodiment of the present invention to include a targeting moiety in at least one of the at least one halogenated xanthene active ingredients, such targeting moiety being selected from a group that includes deoxyribonuceic acid (DNA), ribonuclerc acid (RNA), amino acids, proteins, antibodies, ligands, haptens, carbohydrate receptors, carbohydrate complexing agents, lipid receptors, lipid complexing agents, protein receptors, protein complexing agents, chelators, encapsulating vehicles, short-chain aliphatic hydrocarbons, long-chain aliphatic hydrocarbons, aromatic hydrocarbons, aldehydes, ketones, alcohols, esters, amides, amines, nitriles, azides, hydrophilic moieties, and hydrophobic moieties. A further example of this embodiment is derivatization of Rose Bengal with a lipid (at position $R^1$, via esterification), so as to increase the lipophilicity of Rose Bengal, and thereby modify its targeting properties in a patient. An additional further example of this embodiment is derivatization of Rose Bengal with folate (at position $R^1$, via esterification or other modes of attachment), so as to increase selective targeting of cancer and other cells exhibiting enhanced folate receptor activity or folate metabolism.

As a further example of the desirable chemical, biochemical, and physical properties of the halogenated xanthenes and halogenated xanthene derivatives, the inventors of the present invention have shown that such agents exhibit a remarkable combination of low dark cytotoxicity and highlight cytotoxicity. This is evidenced by the following results: intracorporeal administration of a medicament containing Rose Bengal into tumor-bearing laboratory animals at levels equivalent to or greater than 100 mg/kg resulted in negligible biological effects in the absence of irradiation; however, irradiation of tumor tissue in such animals subsequent to such administration resulted in marked destruction of such tumor tissue. Further, as previously described, the inventors of the present invention have shown that such agents are readily cleared from healthy tissues in a matter of several hours, and are known to be rapidly excreted in bile, urine and feces, without doing damage to those healthy tissues while it was there. This is in dramatic contrast to many conventional radiodense agents, some of which exhibit half-lives in healthy tissues on the order of many weeks.

Further examples of the desirable properties of the halogenated xanthenes and halogenated xanthene derivatives are as follows: the halogenated xanthenes and halogenated xanthene derivatives are easily synthesized using simple low-cost synthetic methods, can be readily purified, and exhibit excellent stability (such as a long shelf life without need for refrigeration or an inert atmosphere).

Because the halogenated xanthenes and their derivatives are, in general, fine solid powders in their pure form, it is preferred that, for proper delivery to desired tissues, such agents be formulated in appropriate delivery vehicles. Approaches to such formulation will be generally known to those of ordinary skill in the art. Specifically, such formulations are preferred so as to facilitate agent delivery into the body and subsequent contact with, and delivery to, desired tissues to be treated.

It is thus a further embodiment of the present invention that at least one halogenated xanthene or halogenated xanthene derivative be formulated as an intracorporeal medicament in a form suitable for intracorporeal administration via various conventional modes and routes. Such suitable forms include medicaments formulated in a liquid, semisolid, solid or aerosol delivery vehicle, including aqueous suspensions, non-aqueous suspensions, solutions, creams, ointments, gels, syrups, micro-droplet sprays, suppositories, tablets and capsules. The at least one halogenated xanthene or halogenated xanthene derivative may be dissolved or suspended in such delivery vehicle, wherein this vehicle may, in addition to the at least one halogenated xanthene or halogenated xanthene derivative, include various builders, stabilizers, emulsifiers or dispersants, preservatives, buffers, electrolytes, and tissue penetrating or softening agents. Such components of the delivery vehicle may be present as the primary component (by weight or volume) of the medicament, or as a minor component that serves in an adjuvant role in agent delivery with no adverse affect on tissue or treatment outcome.

For example, appropriate builders include cellulose and cellulose derivatives, such as starch, and alginates.

Examples of appropriate stabilizers, emulsifiers or dispersants include liposomes, nanoparticulates and nanodispersions, microparticulates and microdispersions, as well as various lipids, detergents and other surfactants.

Examples of appropriate preservatives include benzalkonium chloride, thimerosal, quaternary amines and urea.

Examples of appropriate buffers include monobasic or dibasic phosphate salts, citrate salts, bicarbonate salts, and ethanolamine.

Examples of appropriate electrolytes include sodium, potassium, calcium and magnesium chlorides, phosphates, and nitrates.

Examples of appropriate tissue penetrating, softening or solvating agents and adjuvants include:

various sulfoxides, such as DMSO and decylmethylsulfoxide;

various aliphatic and fatty alcohols, such as ethanol, propanol, hexanol, octanol, benzyl alcohol, decyl alcohol, lauryl alcohol, and stearyl alcohol;

various linear and branched, saturated and unsaturated fatty acids, such as lauric acid, caproic acid, capric acid, myristic acid, stearic acid, oleic acid, isovaleric acid, neopentanoic acid, trimethyl hexanoic acid, neodecanoic acid and isostearic acid;

various aliphatic and alkyl fatty acid esters, such as isopropyl n-butyrate, isopropyl n-hexanoate, isopropyl n-decanoate, isopropyl myristate, isopropyl palmitate, octyldodecyl myristate, ethyl acetate, butyl acetate, methyl acetate, methylvalerate, methylpropionate, diethyl sebacate and ethyl oleate;

various polyols, such as propylene glycol, polyethylene glycol, ethylene glycol, diethylene glycol, triethylene glycol, diproplyene glycol, glycerol, propanediol, butanediol, pentanediol and hexanetriol;

various amides, such as urea, dimethylacetamide, diethyltoluamide, dimethylformamide, dimethyloctamide, dimethyldecamide; biodegradable cyclic urea, such as 1-alkyl-4-imidazolin-2-one; pyrrolidone derivatives, such as 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methyoxycarbonyl-2-pyrrolidone, 1-methyl-4-methyoxycarbonyl-2-pyrrolidone, 1-lauryl-4-methyoxycarbonyl-2-pyrrolidone, N-cyclohexylpyrrolidone, N-dimethylaminopropylpyrrolidone, N-cocoalkypyrrolidone, N-tallowalkylpyrrolidone; biodegradable pyrrolidone derivatives, such as fatty acid esters of N-(2-hyroxyethyl)-2-pyrrolidone; cyclic amides, such as 1-dodecylazacycloheptane-2-one (Azone®), 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11-trimethydodecyl)azacycloheptan-2-one, 1-geranylazacyclohexane-2-one, 1-geranylazacyclopentan- 2,5-dione, 1-farnesylazacyclopentan-2-one; hexamethylenelauramide and its derivatives; and diethanolamine and triethanolamine;

various surfactants, such as anionic surfactants, including sodium laurate and sodium lauryl sulfate; cationic surfactants, including cetyltrimethyl ammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride; nonionic surfactants, such as Polaxamer (231, 182, 184), Brij (30, 93, 96, 99), Span (20, 40, 60, 80, 85), Tween (20, 40, 60, 80), Myrj (45, 51, 52), Miglyol 840; various bile salts, such as sodium cholate, sodium salts of taurocholic, glycholic, desoxycholic acids; lecithin;

various terpenes, including hydrocarbons, such as D-limonene, α-pinene, β-carene; various terpene alcohols, including α-Terpineol, terpinen-4-ol, carvol; various terpene ketones, including carvone, pulegone, piperitone, menthone; various terpene oxides, including cyclohexane oxide, limonene oxide, α-pinene oxide, cyclopentene oxide, 1,8-cineole; various terpene oils, including ylang ylang, anise, chenopodium, eucalyptus;

various alkanones, such as N-heptane, N-octane, N-nonane, N-decane, N-undecane, N-dodecane, N-tridecane, N-tetradecane, N-hexadecane;

various organic acids, such as salicylic acid and salicylites (including their methyl, ethyl, and propyl glycol derivatives), citric and succinic acid.

The present invention is not limited to the above recited examples, as other formulations familiar to those of ordinary skill in the art, including various simple or complex combinations of vehicles and adjuvants, will be useful for improving delivery of the radiodense component to the medicament to target tissues and are contemplated as being included within the present invention.

2. Methods and Medical Use of the Subject Medicament for High Energy Phototherapeutic Treatment of Conditions Affecting the Skin and Related Organs.

The inventors have discovered that the intracorporeal medicaments disclosed herein are broadly applicable to improved high energy phototherapeutic treatment of various conditions affecting the skin and related organs of humans and animals. The medicament can be applied, using conventional intracorporeal administration modes, directly or indirectly to, or substantially proximal to, tissues to be treated, including those of the skin, nails and scalp. Such administration modes provide direct delivery of medicament to, into or substantially proximal to, tissues to be treated, or systemic delivery of medicament to, into or substantially proximal to, tissues to be treated.

Example indications include treatment for: Psoriasis and Pustular Psoriasis; Reiter's Syndrome; Skin Ulcers, including Stasis Dermatitis, Stasis Ulcers, Ischemic Ulcers, Sickle Cell Leg Ulcers, Diabetic Ulcers, Inflammatory Ulcers; Eczematous Disease and Eczematous Reaction; various Ichthyoses; Atopic Dermatitis; Superficial Wrinkles; Near Surface Fat Reduction; Benign and Malignant Proliferative Disorders, such as Benign Epithelial Tumors and Hamartomas; Premalignant and Malignant Epithelial Tumors, including Actinic Keratoses, Basal Cell Carcinoma, Squamous Cell Carcinoma, and Keratoacanthoma; Benign and Malignant Adnexal Tumors; Tumors of Pigment-Producing Cells, including Malignant Melanoma, Solar Lentigines, Nevi, and Café-au-lait; Sarcomas; Lymphomas; Metastatic Tumors, such as Metastases of Melanoma, Breast or Other Tumors to the Skin and Related Organs; Vascular Disorders, such as Hemangiomas and Port Wine Stain; Microbial Infection, such as Bacterial, Fungal, Yeast, Parasitic or Other Infections; Warts; and Acne. These examples are provided for illustrative purposes, as the present invention is not limited to the recited examples and includes other indications known to those skilled in the art.

In an example of a preferred embodiment of this method of treatment or medical use, the inventors have discovered that intratumoral injection of a medicament solution containing Rose Bengal at a concentration of approximately 1–10% W/V into mice exhibiting radiation resistant cutaneous melanoma tumors, followed by irradiation of such tumors with x-rays, gamma rays, or other ionizing radiation, leads to substantial or complete high energy phototherapeutic eradication of such tumors. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of the skin and related organs of humans and animals and are included within the present invention.

3. Methods and Medical Use of the Subject Medicament for High Energy Phototherapeutic Treatment of Conditions Affecting the Mouth and Digestive Tract and Related Organs.

The inventors have discovered that the intracorporeal medicaments disclosed herein are broadly applicable to improved high energy phototherapeutic treatment of various conditions affecting the mouth and digestive tract and related organs of humans and animals. The medicament can be applied, using conventional intracorporeal administration modes, directly or indirectly to, or substantially proximal to, tissues to be treated, including those of the mouth, gums, tongue, larynx, pharynx, esophagus, stomach, intestines and colon. Such administration modes provide direct delivery of medicament to, into or substantially proximal to, tissues to be treated, or systemic delivery of medicament to, into or substantially proximal to, tissues to be treated.

Example indications include treatment for: Benign Esophageal Lesions, Barretts Esophagus and other Esophageal Hyperplasia and Dysplasia, and Esophageal Cancer, including Squamous Cell Carcinoma, Adenocarinoma, Carsinosarcoma, Pseudosarcoma, and Sarcoma; Gastric Ulcers, Leiomyomas, Polyps, Neoplasms, Lymphoma and Pseudolymphoma, Adenocarcinoma, Primary Lymphoma, Leiomyosarcoma; Oral and Oropharynx Cancer and Premalignancies, Ulcers and Inflammatory Lesions, including Squamous Cell Carcinoma, Lymphoma, Actinic Cheilitis, Nicotine Stomatitis, Leukoplakia, Erythroplakia; Gum and Other Peridontal Disease, including Gingivitis; Laryngeal Hyperplasia, Dysplasia and Neoplasms; Colorectal Cancer, Hyperplasia, Dysplasia and Polyps; and Metastatic Tumors, such as Metastases of Melanoma, Breast or Other Tumors to tissues of the Mouth and Digestive Tract and Related Organs. These examples are provided for illustrative purposes, as the present invention is not limited to the recited examples and includes other indications known to those skilled in the art.

In an example of a preferred embodiment of this method of treatment or medical use, the inventors have found that intratumoral injection of a medicament solution containing Rose Bengal at a concentration of approximately 1–10% W/V into mice and other animals exhibiting tumors of various types, followed by irradiation of such tumors with x-rays, gamma rays, or other ionizing radiation, leads to substantial or complete high energy phototherapeutic destruction of tumors in the treated region. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of the mouth and digestive tract and related organs of humans and animals and are included within the present invention.

4. Methods and Medical Use of the Subject Medicament for High Energy Phototherapeutic Treatment of Conditions Affecting the Urinary and Reproductive Tracts and Related Organs.

The inventors have discovered that the intracorporeal medicaments disclosed herein are broadly applicable to improved high energy phototherapeutic treatment of various conditions affecting the urinary and reproductive tract and related organs of humans and animals. The medicament can be applied, using conventional intracorporeal administration modes, directly or indirectly to, or substantially proximal to, tissues to be treated, including those of the urethra, bladder, ureter, kidneys, vulva, vagina, cervix, uterus, fallopian tubes, ovaries, penis, testes, vas deferens, prostate, epididymis and breast. Such administration modes provide direct delivery of medicament to, into or substantially proximal to, tissues to be treated, or systemic delivery of medicament to, into or substantially proximal to, tissues to be treated.

Example indications include treatment for: Urinary Tract Disease, including Cancerous and Pre-Cancerous Hyperplasia, Dysplasia and Neoplasms, Tumors and other Growths, Inflammation, and Infection of the Bladder, Ureter, Urethra, and Kidney; Cancerous and Pre-Cancerous Hyperlasia, Dysplasia and Neoplasms, Tumors and other Growths, Inflammation, and Infection of the Cervix, Endometrium, Myometrium, Ovaries, Fallopian Tubes, Uterus, Vulva, and Vagina, including Vaginal Warts; Cancerous and Pre-Cancerous Hyperlasia, Dysplasia and Neoplasms, Tumors and other Growths, Inflammation, and Infection of the Prostate and Testes; Cancerous and Pre-Cancerous Hyperlasia, Dysplasia and Neoplasms, Tumors and other Growths, Inflammation, and Infection of the Breast; Metastatic Tumors, such as Metastases of Melanoma, Breast or Other Tumors to tissues of the Urinary and Reproductive Tract and Related Organs; Reproductive Tract Infections, including Tinea Cruris, Candidiasis, Condylomata Acuminata, Molluscum Contagiosum, Genital Herpes Simplex Infection, Lymphogranuloma Venereum, Chancroid, Granuloma Inguinale, Erythrasma; Psoriais; and Lichen Planus and Lichen Sclerosus. These examples are provided for illustrative purposes, as the present invention is not limited to the recited examples and includes other indications known to those skilled in the art.

In an example of a preferred embodiment of this method of treatment or medical use, the inventors have discovered that intratumoral injection of a medicament solution containing Rose Bengal at a concentration of approximately 1–10% W/V into mice and other animals exhibiting tumors of various types, followed by irradiation of such tumors with x-rays, gamma rays, or other ionizing radiation, leads to substantial or complete high energy phototherapeutic eradication of such tumors. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of the urinary and reproductive tract and related organs of humans and animals and are included within the present invention.

5. Methods and Medical Use of the Subject Medicament for High Energy Phototherapeutic Treatment of Conditions Affecting the Respiratory Tract and Related Organs.

The inventors have discovered that the intracorporeal medicaments disclosed herein are broadly applicable to improved high energy phototherapeutic treatment of various conditions affecting the respiratory tract and related organs of humans and animals. The medicament can be applied, using conventional intracorporeal administration modes, directly or indirectly to, or substantially proximal to, tissues to be treated, including those of the lung and alveoli, bronchi, trachea, hypopharynx, larynx, nasopharynx, tear ducts, sinuses and nasal cavities. Such administration modes provide direct delivery of medicament to, into or substantially proximal to, tissues to be treated, or systemic delivery of medicament to, into or substantially proximal to, tissues to be treated.

Example indications include treatment for: Hyperplasia, Dysplasia and Neoplasia, Cancer. Inflammation and Infection of the Nasal Cavity, Paranasal Sinuses, Tear Ducts, Eustachian Tubes, Nasopharynx, Hypopharynx, Larynx, Trachea, Bronchi, Lung and Alveoli; and Metastatic Tumors, such as Metastases of Melanoma, Breast or Other Tumors to tissues of the Respiratory Tract and Related Organs. These examples are provided for illustrative purposes, as the present invention is not limited to the recited examples and includes other indications known to those skilled in the art.

In an example of a preferred embodiment of this method of treatment or medical use, the inventor have discovered that intratumoral injection of a medicament solution containing Rose Bengal at a concentration of approximately 1–10% W/V into mice and other animals exhibiting tumors of various types, followed by irradiation of such tumors with x-rays, gamma rays, or other ionizing radiation, leads to substantial or complete high energy phototherapeutic eradication of such tumors.

The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic treatment of the respiratory tract and related organs of humans and animals and are included within the present invention.

6. Methods and Medical Use of the Subject Medicament for High Energy Phototherapeutic Treatment of Conditions Affecting the Circulatory System and Related Organs.

The inventors have discovered that the intracorporeal medicaments disclosed herein are broadly applicable to improved high energy phototherapeutic treatment of various conditions affecting the circulatory system and related organs of humans and animals. The medicament can be applied, using conventional intracorporeal administration modes, directly or indirectly to, or substantially proximal to, tissues to be treated, including those of the heart, kidneys, liver and blood vessels. Such administration modes provide direct delivery of medicament to, into or substantially proximal to, tissues to be treated, or systemic delivery of medicament to, into or substantially proximal to, tissues to be treated.

Example indications include treatment for: Hyperplasia, Dysplasia and Neoplasia, Cancer, Inflammation and Infection of the Kidneys and Liver; Metastatic Tumors, such as Metastases of Melanoma, Breast or Other Tumors to tissues of the Circulatory System and Related Organs; Disease of Cardiac and Pericardial Tissues and Circulatory Tissues, including Arteries and Veins, including Plaques and Infections of such tissues, such as Bacterial Endocarditis; and destruction of unwanted blood vessels, such as spider veins. These examples are provided for illustrative purposes, as the present invention is not limited to the recited examples and includes other indications known to those skilled in the art.

In an example of a preferred embodiment of this method of treatment or medical use, the inventors have discovered that intratumoral injection of a medicament solution containing Rose Bengal at a concentration of approximately 1–10% W/V into mice and other animals exhibiting tumors of various types, followed by irradiation of such tumors with x-rays, gamma rays, or other ionizing radiation, leads to substantial or complete high energy phototherapeutic eradication of such tumors. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic treatment of the circulatory system and related organs of humans and animals and are included within the present invention.

7. Methods and Medical Use of the Subject Medicament for High Energy Phototherapeutic Treatment of Conditions Affecting the Head and Neck.

The inventors have discovered that the intracorporeal medicaments disclosed herein are broadly applicable to improved high energy phototherapeutic treatment of various conditions affecting the head and neck of humans and animals. The medicament can be applied, using conventional intracorporeal administration modes, directly or indirectly to, or substantially proximal to, tissues to be treated, including those of the head, neck, brain, eyes and ears, Such administration modes provide direct delivery of medicament to, into or substantially proximal to, tissues to be treated, or systemic delivery of medicament to, into or substantially proximal to, tissues to be treated.

Example indications include treatment for: Tumors or Resected Tumor Beds of Intra-cranial and other Head and Neck Tumors; Ophthalmic Tumors and other diseases, including Macular Degeneration and Diabetic Retinopathy; Metastatic Tumors, such as Metastases of Melanoma, Breast or Other Tumors to tissues of the Head or Neck. These examples are provided for illustrative purposes, as the present invention is not limited to the recited examples and includes other indications known to those skilled in the art.

In an example of a preferred embodiment of this method of treatment or medical use, the inventors have discovered that intratumoral injection of a medicament solution containing Rose Bengal at a concentration of approximately 1–10% W/V into mice exhibiting tumors of various types, such as radiation resistant metastatic melanomas, followed by irradiation of such tumors with x-rays, gamma rays, or other ionizing radiation, leads to substantial or complete high energy phototherapeutic eradication of such tumors. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of the head and neck of humans and animals and are included within the present invention.

8. Methods and Medical Use of the Subject Medicament for High Energy Phototherapeutic Treatment of Conditions Affecting the Endocrine and Lymphoreticular Systems and Related Organs.

The inventors have discovered that the intracorporeal medicaments disclosed herein are broadly applicable to improved high energy phototherapeutic treatment of various conditions affecting the endocrine and lymphoreticular systems and related organs of humans and animals. The medicament can be applied, using conventional intracorporeal administration modes, directly or indirectly to, or substantially proximal to, tissues to be treated, including those of the thyroid gland, the thalamus and hypothalamus, the pituitary gland, lymph nodes and lymphoreticular system. Such administration modes provide direct delivery of medicament to, into or substantially proximal to, tissues to be treated, or systemic delivery of medicament to, into or substantially proximal to, tissues to be treated.

Example indications include treatment for: Hyperplasia, Dysplasia and Neoplasia, Cancer, Inflammation and Infection of the Thyroid, Thalamus and Hypothalamus, Pituitary Gland, Lymph Nodes and Lymphoreticular system, including Graves' Disease; and Metastatic Tumors, such as Metastases of Melanoma, Breast or Other Tumors to tissues of the Endocrine and Lymphoreticular Systems and Related Organs. These examples are provided for illustrative purposes, as the present invention is not limited to the recited examples and includes other indications known to those skilled in the art.

In an example of a preferred embodiment of this method of treatment or medical use, the inventors have discovered that intratumoral injection of a medicament solution containing Rose Bengal at a concentration of approximately 1–10% W/V into mice and other animals exhibiting tumors of various types, followed by irradiation of such tumors with x-rays, gamma rays, or other ionizing radiation, leads to substantial or complete high energy phototherapeutic eradication of such tumors. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic treatment of the endocrine and lymphoreticular systems and related organs of humans and animals and are included within the present invention.

9. Methods and Medical Use of the Subject Medicament for High Energy Phototherapeutic Treatment of Conditions Affecting Various Other Tissues, Such as Connective Tissues and Various Tissue Surfaces Exposed During Surgery The inventors have discovered that the intracorporeal medicaments disclosed herein are broadly applicable to improved high energy phototherapeutic treatment of various conditions affecting various other internal or external tissues of humans and animals, such as connective tissues and various tissue surfaces exposed during surgery. The medicament can be applied, using conventional intracorporeal administration modes, directly or indirectly to, or substantially proximal to, tissues to be treated, including those of tissue surfaces exposed during surgery, including endoscopic surgery or other endoscopic procedures. Such application modes provide direct delivery of medicament to, into or substantially proximal to, tissues to be treated, or systemic delivery of medicament to, into or substantially proximal to, tissues to be treated.

Example indications include treatment for: Joint Inflammation, such as that of Arthritis, Resected Tumor Beds of Thoracic, Abdominal, or other Tumors; Metastatic Tumors, such as Metastases of Breast Tumors to the Skin; Tumors or Infections of the Pleura, Peritoneum or Pericardium; Metastatic Tumors, such as Metastases of Melanoma, Breast or Other Tumors to Connective Tissues and various Tissue Surfaces exposed during surgery; and various other substantially similar indications. These examples are provided for illustrative purposes, as the present invention is not limited to the recited examples and includes other indications known to those skilled in the art.

In an example of a preferred embodiment of this method of treatment or medical use, the inventors have discovered that intratumoral injection of a medicament solution containing Rose Bengal at a concentration of approximately 1–10% W/V into mice and other animals exhibiting tumors of various types, followed by irradiation of such tumors with x-rays, gamma rays, or other ionizing radiation, leads to substantial or complete high energy phototherapeutic eradication of such tumors. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of conditions affecting various other tissues of humans and animals, such as connective tissues and various tissue surfaces exposed during surgery and are included within the present invention.

10. Methods and Medical Use of the Subject Medicament for High Energy Phototherapeutic Treatment of Conditions Related to Microbial, Viral, Fungal or Parasitic Infection The inventors have discovered that the intracorporeal medicaments disclosed herein are broadly applicable to improved high energy phototherapeutic treatment of various conditions related to microbial, viral, fungal or parasitic infection of humans and animals. The medicament can be applied, using conventional intracorporeal administration modes, directly or indirectly to, or substantially proximal to, tissues to be treated, including those of tissue surfaces exposed during surgery, including endoscopic surgery or other endoscopic procedures. Such administration modes provide direct delivery of medicament to, into or substantially proximal to, tissues to be treated, or systemic delivery of medicament to, into or substantially proximal to, tissues to be treated.

Example indications include treatment for: Bacterial and Antibiotic Resistant Bacterial Infection, including those caused by Gram Positives and Gram Negatives, Streptomycetes, Actinomycetes, Staphylococci, Streptococci, Pseudomonas, *Escherichia coli*, Mycobacteria and others; Infection caused by Filamentous Fungi and Non-filamentous Fungi like Cryptosporidium, Histoplasma, Aspergillus, Blastomyces, Candida and others; Parasitic Infection caused by Amoeba (including for use in lysing and killing amoeba in amoebic cysts), Trichinella, Dirodfilaria (Heart worm in dogs) and various other substantially similar indications.

These examples are provided for illustrative purposes, as the present invention is not limited to the recited examples and includes other indications known to those skilled in the art.

In an example of a preferred embodiment of this method of treatment or medical use, the inventors have discovered that application of an aqueous solution containing Rose Bengal at a concentration of approximately 1 to 10 micromolar to antibiotic resistant *Staphylococcus aureus, Escherichia coli*, various other gram positive and gram negative bacteria, and various yeasts, results in accumulation of such Rose Bengal in such organisms; subsequent irradiation leads to substantial or complete eradication of such microbes. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of microbial, viral, fungal or parasitic infection of humans and animals and are included within the present invention.

TABLE 1

Chemical and Physical Properties of Some Example Halogenated Xanthenes.

| Compound | Substitution | | | | | MW (g) |
| --- | --- | --- | --- | --- | --- | --- |
| | X | Y | Z | $R^1$ | $R^2$ | |
| Fluorescein | H | H | H | Na | Na | 376 |
| 4',5'-Dichlorofluorescein | Cl | H | H | Na | Na | 445 |
| 2',7'-Dichlorofluorescein | H | Cl | H | Na | Na | 445 |
| 4,5,6,7-Tetrachlorofluorescein | H | H | Cl | H | H | 470 |
| 2',4',5',7'-Tetrachlorofluorescein | Cl | Cl | H | Na | Na | 514 |
| Dibromofluorescein | Br | H | H | Na | Na | 534 |
| Solvent Red 72 | H | Br | H | H | H | 490 |
| Diiodofluorescein | I | H | H | Na | Na | 628 |
| Eosin B | $NO_2$ | Br | H | Na | Na | 624 |
| Eosin Y | Br | Br | H | Na | Na | 692 |
| Ethyl Eosin | Br | Br | H | $C_2H_5$ | K | 714 |
| Erythrosin B | I | I | H | Na | Na | 880 |
| Phloxine B | Br | Br | Cl | Na | Na | 830 |
| Rose Bengal | I | I | Cl | Na | Na | 1018 |
| Rose Bengal Lithium Salt | I | I | Cl | Li | Li | 986 |
| Rose Bengal Derivative I | I | I | Cl | $C_2H_5$ | $(C_2H_4)_3NH$ | 1100 |
| Rose Bengal Derivative II | I | I | Cl | $(C_2H_5)_3NH$ | $(C_2H_4)_3NH$ | 1166 |
| 4,5,6,7-Tetrabromoerythrosin | I | I | Br | Na | Na | 1195 |

TABLE 2

Partition coefficients for several halogenated xanthenes; $K_p$ is the ratio of equilibrium concentrations of agent in a lipophilic phase (n-octanol) contacted with an aqueous phase (saline).

| Agent | $K_p$ |
| --- | --- |
| Phloxine B | 1.1 |
| Erythrosin B | 1.9 |
| Rose Bengal | 11.5 |

This description has been offered for illustrative purposes only and is not intended to limit the invention of this application, which is defined in the claims below.

We claim:

1. A method of treating diseased tissue from disorders selected from the group consisting of hyperplasia, dysplasia, neoplasia, benign tumors, malignant tumors, resected tumor beds, benign proliferative disorders, malignant proliferative disorders, vascular plaque, inflammation, and infection of human or animal tissue comprising:

administering an intracorporeal radiosensitizer medicament having an active ingredient consisting of at least one halogenated xanthene into or proximate to said human or animal tissue, wherein said halogenated xanthene contains at least four halogen atoms selected from the group consisting of iodine and bromine; and applying ionizing radiation to said human or animal tissue, wherein said applied ionizing radiation is selected from the group consisting of x-rays, gamma rays, and ionizing radiation having an energy greater than 1 keV and less than 1000 MeV, and wherein said medicament present within or proximate to said tissue increases the efficiency of conversion of said applied ionizing radiation into localized therapeutic effects.

2. The method of claim 1 wherein said human or animal tissue comprises the skin, the mouth and digestive tract, the urinary and reproductive tracts, the respiratory tract, the circulatory system, the head and neck, the endocrine and lymphoreticular systems, connective tissue, tissue surfaces exposed during surgery, and tissue with microbial, viral, fungal, or parasitic infection.

3. The method of claim 1 wherein said halogenated xanthene is Rose Bengal.

4. The method of claim 1 wherein said halogenated xanthene is 4,5,6,7-Tetrabromoerythrosin.

* * * * *